United States Patent [19]

Berke

[11] Patent Number: 4,459,358
[45] Date of Patent: Jul. 10, 1984

[54] MULTILAYER ELEMENT FOR ANALYSIS

[75] Inventor: Carl M. Berke, Cambridge, Mass.

[73] Assignee: Polaroid Corporation, Cambridge, Mass.

[21] Appl. No.: 454,141

[22] Filed: Dec. 29, 1982

[51] Int. Cl.³ .................... G01N 31/22; G01N 33/52; G01N 33/54; G01N 33/58
[52] U.S. Cl. .................... 436/170; 422/56; 435/805; 436/810
[58] Field of Search .............. 422/56, 57; 435/805; 436/86, 87, 88, 57, 169, 170, 172, 810

[56] References Cited

U.S. PATENT DOCUMENTS

| | | |
|---|---|---|
| 3,723,064 | 3/1973 | Liotta . |
| 3,992,158 | 11/1976 | Przybylowicz et al. . |
| 4,042,335 | 8/1977 | Clement . |
| 4,050,898 | 9/1977 | Goffe et al. . |
| 4,066,403 | 1/1978 | Bruschi . |
| 4,069,016 | 1/1978 | Wu . |
| 4,144,306 | 3/1979 | Figueras ............ 436/170 X |
| 4,166,093 | 8/1979 | Smith-Lewis et al. ....... 422/56 |
| 4,258,001 | 3/1981 | Pierce et al. ............ 422/56 |
| 4,292,272 | 9/1981 | Kitajima et al. ........... 422/57 |

FOREIGN PATENT DOCUMENTS 81108364.1 5/1982 European Pat. Off. .

OTHER PUBLICATIONS

Ouchterlony et al., Immunochemistry, Third ed. Blackwell Scientific Publication, Oxford, England, vol. 1 Chapter 19.

Primary Examiner—Arnold Turk
Assistant Examiner—Robert J. Hill, Jr.
Attorney, Agent, or Firm—Philip G. Kiely

[57] ABSTRACT

A multilayer element for the analysis of a liquid containing an analyte comprising a reaction layer which retains a predetermined amount of a diffusible reagent containing a detectable species; said reagent adapted to be rendered substantially non-diffusible by said analyte as a function of the concentration of said analyte; a registration layer adapted to receive reagent diffusing thereto; means for detecting said reagent in said registration layer and an insulating layer intermediate said reaction layer adapted to provide discrimination between detectable species in said reagent layer and said registration layer.

16 Claims, 3 Drawing Figures

Ag = ANTIGEN
Ab* = ANTIBODY WITH DETECTABLE SPECIES
Ab*-Ag = PRECIPITATED ANTIGEN-ANTIBODY COMPLEX
M = CONCENTRATING OR IMMOBILIZING AGENT

MULTILAYER ELEMENT FOR ANALYSIS

BACKGROUND OF THE INVENTION

A number of devices are known for the chemical analysis of substances in liquids, especially biological liquids. One type of device requires expensive equipment, highly trained operators and a large volume of samples for analysis.

Another type of device is a relatively simple, portable, multilayer element for carrying out a single test at a time without expensive equipment.

U.S. Pat. No. 3,723,064, issued Mar. 23, 1973, is directed to a layered testing device comprising a layer impregnated with a chemical reagent for a reaction with the substance under test comprising a permeable member having first and second regions of different permeabilities to the test fluid. A transmission layer is placed adjacent the permeable member to aid in drawing the reaction products resulting from the reaction of the chemical reagent and the substance under test through to the next layer, which is an indicator layer, impregnated with a chemical adapted to react with the above-mentioned reaction products to produce a visual reaction indicative of the presence and concentration of the substance under test.

U.S. Pat. No. 3,992,158, issued Nov. 16, 1976, discloses an integral analytical element containing a spreading layer and a reagent layer. The spreading layer is an isotropically, non-fibrous porous layer which spreads within itself at least a component of the applied liquid sample to obtain a uniform concentration which then passes into the adjacent reagent layer where it can react to form a detectable species.

U.S. Pat. No. 4,042,335, issued Aug. 16, 1977, is directed to a multilayer element for the analysis of liquids such as biochemical and biological liquids. The element comprises a reagent layer which includes a composition that is interactive with the substance to be analyzed to provide a diffusible, detectable species; and a registration layer that is permeable to the detectable species and within which such species can be detected. The element can also include a spreader layer and a radiation blocking layer to enhance detection of the detectable species.

U.S. Pat. No. 4,050,898, issued Sept. 27, 1977, is directed to an analytical element comprising at least two superposed layers, a spreading layer and reagent layer, wherein the spreading layer is a non-fibrous, isotropically porous spreading layer of water-resistant material which includes a non-ionic surfactant to normalize transport in the spreading layer.

U.S. Pat. No. 4,066,403, issued Jan. 3, 1976 is directed to an integral analytical element for analyzing complex fluids which comprises a first reagent for reacting with an analyte to produce a decomposition product and a second reagent adapted to react with said decomposition product to produce a detectable change wherein a barrier to said decomposition product is disposed between the first and second reagents which is substantially impermeable to interferants.

U.S. Pat. No. 4,069,016, issued Jan. 17, 1978, is directed to a method for determining bilirubin in an aqueous liquid sample which comprises contacting said sample with a composition containing a diffusible, bilirubin-displaceable, detectable ligand bound to a carrier which can also bind bilirubin, and detecting the thus-displaced detectable ligand.

U.S. Pat. No. 4,144,306, issued Mar. 13, 1979, is directed to a displacement/release method employing a multilayer analytical element comprising at least a reagent layer and a registration layer wherein the reagent layer contains an interactive composition including a non-diffusible material having a preformed detectable moiety bound thereto, which composition, in the presence of a liquid containing an analyte, provides a diffusible product comprising the preformed detectable moiety by displacement by the analyte. The registration layer receives the diffusible product. Other layers may also be employed, including supports, spreader layers, radiation blocking layers, and the like. As an example of said interactive composition, mention is made of a tagged antigen-antibody complex wherein the analyte displaces the tagged member which migrates to the registration layer.

U.S. Pat. No. 4,166,093, issued Aug. 28, 1979, is directed to an element for the analysis of liquids which include a radiation-transmissive reagent layer containing a composition interactive with an analyte to provide a radiometrically detectable species, a porous radiation blocking layer permeable to the analyte and a radiation-transmissive, detectable species migration inhibiting layer interposed between the reagent layer and the radiation-blocking layer, said detectable species migration-inhibiting layer being permeable to said analyte and inhibiting the migration of said radiometrically detectable species to said porous radiation blocking layer upon contact of said element with the liquid under analysis.

U.S. Pat. No. 4,258,001, issued Mar. 24, 1981, is directed to a multilayer element for competitive immunoassay which includes a zone having a particulate structure which comprises heat-stable, non-swellable organo-polymeric particles and an adhesive. An immunoreagent, such as a fluorescent-labelled antigen, may be bound to the particles. In Example 50, a competitive immunoassay element is described wherein an antibody is immobilized in a spreading/reagent zone dispersion and labeled antigen is premixed before application to the test element. It is also stated that the labelled antigen may be incorporated into the element. However, it is stated (col. 30, lines 2 to 7) that where the labelled antigen is incorporated in the element, care should be taken to maintain the labelled antigen apart from the immobilized antibody which is also in the element to avoid premature binding of labelled antigen to antibody.

*Immunochemistry*, D. M. Weir, Third Edition, Blackwell Scientific Publication, Oxford, England, Vol. 1, Chapter 19, describes a radial, quantitative immunoprecipitation technique wherein an analyte containing an antigen is placed in the center of a layer of colloid containing an antibody. The distance the antigen radiates from the center is measured to provide a quantitative determiation of the antigen in the analyte.

European Patent Application No. 0 051 183, filed Oct. 15, 1981 discloses a multilayer analysis element comprising a porous medium layer to which an antigen (or antibody) is immobilized and a layer through which substances which did not participate in the immunoprecipitation in the porous medium layer can diffuse, whereupon detection means can be employed to determine the quantity of said substances. In operation, an antigen (or antibody) to be analyzed for is labelled and then applied to the porous medium layer. The labeled antigen (or antibody) reacts with the immobilized antibody (or antigen) to form a complex. Excess, unreacted antigen (or antibody) is inherently separated from the complex and diffused into the reagent layer. Unreacted labelled antigen (or antibody) is optically measured to provide a quantitative determination. This patent application demonstrates the quantitative nature of gel-mediated precipitation reactions.

SUMMARY OF THE INVENTION

A multilayer element for the analysis of a liquid containing an analyte comprising a reaction layer containing a predetermined amount of a diffusible reagent containing a detectable species; said reagent adapted to be rendered substantially non-diffusible by said analyte as a function of the concentration of said analyte; a registration layer adapted to receive reagent diffusing thereto; means for detecting said reagent in said registration layer and an insulating layer intermediate said reaction layer adapted to provide discrimination between detectable species in said reagent layer and said registration layer.

DETAILED DESCRIPTION OF THE INVENTION

Figure 1:
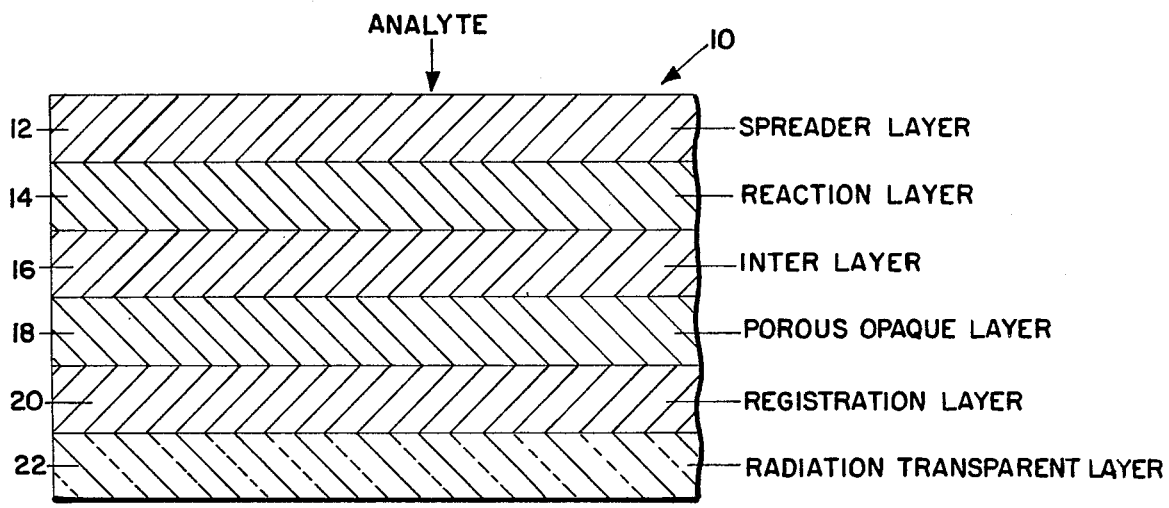
FIG. 1 is a schematic, cross-sectional view of a preferred multilayer element of the present invention.

The present invention contemplates an analytical technique which involves a predetermined concentration of a reagent in a layer of the analytical element which is adapted to react with an analyte. Thus, the analyte will react with and immobilize a quantity of reagent, which is normally diffusible, in a relationship to the quantity of analyte. The unreacted reagent which also contains a detectable species, diffuses to a registration layer where suitable detection means are employed to ascertain the quantity of reagent in the registration layer by virtue of the detectable species. Preferably, an insulating layer is employed between the reaction layer and registration layer to limit detection of the detectable species to that which has diffused to the registration layer.

Although the present invention is suitable for use in analyzing substantially any substance that can react with a second diffusible substance with a detectable species to immobilize said second substance, the invention is particularly suited for use employing immunoprecipitation techniques. For simplicity, the present invention will be described in detail in terms of immunoprecipitation.

Analytical techniques may be classified as heterogeneous or homogeneous methods. Heterogeneous methods require physical separation of free and bound reactants but are considered to be more sensitive. Homogeneous methods are preferred for their ease and simplicity of operation but suffer from high background levels caused by incomplete discrimination between bound and free species. In a homogeneous method physical separation does not occur but rather a modulation of one of the reactant labels based on the carrier's state of complexation. The diminished level of sensitivity is due, at least in part, to incomplete discrimination.

The present invention employs a heterogeneous immunoprecipitation analytical technique in an integral, one-step format, thus obtaining the simplicity of operation of a homogeneous technique with the sensitivity of the heterogeneous technique in a thin film format.

The novel element and procedure of the present invention employs immunoprecipitation techniques in a single step and in a preformed thin film format to effect separation of bound/unbound species and detection is accomplished by differential diffusion of a detectable, labelled antibody, thereby obviating the need for competitive reaction with additional antigen species. Thus, by means of the present invention any substance that produces an immune complex can be analyzed without the employment of reactants other than those producing the immune complex.

The term "immune complex", as used herein, is intended to refer to an aggregate of immunoglobin with its associated ligand in any proportion from antibody excess to antigen excess, either soluble or insoluble, including haptenic or multivalent antigen, and heterogeneous or monoclonal antibody.

In operation, a predetermined amount of sample liquid containing the analyte is brought into contact with a measured amount of a diffusible antibody disposed in a preformed thin film wherein the diffusible antibody contains a detectable species bonded thereto. The antigen analyte associates with the antibody forming a complex species which is substantially less diffusible than the uncomplexed antibody, quantitatively in proportion to the concentration of antigen in the sample liquid. Separation of the complexed and uncomplexed antibody occurs by virtue of the differential in diffusiblity of the uncomplexed antibody which is in excess of that required to complex with the antigen. Determination of the quantity of uncomplexed antibody is carried out by measuring the quantity of antibody which diffuses out of the layer in which it is initially disposed, preferably to a registration layer where it is concentrated by immobilization to prevent any back-diffusion or wandering of the antibody in the element. Measurement is carried out by a procedure that determines the quantity of detectable species in the registration layer which indicates the quantity of antibody-antigen complex species and, therefore, the concentration of antigen analyte in the sample liquid.

Although the present invention is described primarily in terms of analyzing for an antigen employing a diffusible antibody having a detectable species bonded thereto, it should be understood that since immunoprecipitation techniques are employed, an antibody can be analyzed for employing a diffusible antigen with a detectable species bonded thereto. For simplicity, the present invention is described in terms of the antigen as the analyte but it should be understood that the invention encompasses both procedures.

The following example illustrates the principle of thin-film immunoprecipitation.

EXAMPLE 1

The following materials were coated on 3 mil polystyrene base (sold under the trademark TRYCITE by Dow Chemical Co., Midland, MI), 10 mg/ft$^2$ fluorescent labelled immunoglobulin (FITC-anti-human albumin sold by Atlantic Antibodies, Inc., Scarborough, ME), 1000 mg/ft$^2$ agarose (SEAKEM LE, sold by FMC Marine Colloids, Rockland, ME) and 0.1 mg/ft$^2$ of surfactant (p-nonylphenoxy polyglycidol sold under the tradename OLIN 10G, by Olin Chemical Corp., Stamford, CT). The thus-coated base was dried and cut into 10×1 cm strips. The strips were exposed to antigen (globulin-free human albumin, sold by Sigma Chemical Co., St. Louis, MO), by imbibing part of the strip in a solution of the antigen for a period of 10 min then rinsing for 10 sec in distilled water followed by air drying at room temperature. An antigen concentration series was prepared consisting of 0, 0.5, 1 and 2 mg/ml antigen in phosphate buffered saline. The relative fluorescence intensities of the samples were measured from exposed and unexposed portions of individual sample strips using a FLOUROLOG instrument employing 450 nm excitation, 5 nm slits, 470 to 600 nm emission scan and integrated photon counting mode (Spex Industries, Inc. Metuchen, NJ). Comparison between samples was carried out by calculation of the percent diminution in fluorescence caused by exposure to the antigen solution. Referring to Table 1, below, it well be seen that higher levels of antigen fix higher levels of fluorescent antibody.

TABLE 1

| Sample No. | [Ag] (mg/ml) | Flourescence Intensity (%) |
| --- | --- | --- |
| 1 | 0 | 29.5 |
| 2 | 0.125 | 26.5 |
| 3 | 0.250 | 23.0 |
| 4 | 0.375 | 21.2 |
| 5 | 0.500 | 18.5 |

This example demonstrates that antigen was effectively and measurably reacted with pre-coated antibody in a thin-film layer of preformed colloid and that diffusion of antibody out of the layer, occurs differentially and inversely proportional to the quantity of antigen applied to the layer, thus providing a mechanism for antigen determination.

The novel element of the present invention employs, in its simplest form:
 a sample spreading layer;
 a reaction layer comprising a diffusible antibody having a detectable species bonded thereto;
 a porous layer substantially radiation opaque;
 a registration layer adapted to receive and substantially immobilize said antibody diffusing thereto; and
 a radiation transparent base carrying said layers.

The spreader layer possesses a void volume which retains a constant volume per unit area of liquid after uptake of sample is complete and provides for the precise delivery to the reaction layer of a measured quantity of sample liquid, thus eliminating the need for any dispensing or measuring device. As examples of materials suitable for use as the spreader layer, mention may be made of a fibrous layer having a specific, predetermined void volume, the isotropically porous non-fibrous material disclosed in U.S. Pat. No. 3,992,158, and the fabric of U.S. Pat. No. 4,292,272, issued Sept. 29, 1981.

In an alternative embodiment, the spreader layer may comprise a fibrous coating, of, e.g., organic or inorganic fibers, such as paper, asbestos or potassium titanate.

The reaction layer comprises a hydrophilic colloid which is permeable to the liquid sample, inert to protein, swellable but insoluble to maintain wet-strength integrity and in which the antibody having the detectable species bonded thereto is initially disposed and which is non-reactive and non-binding to said antibody. Suitable materials for the reaction layer include hydrophilic gelable materials including both naturally occurring substances such as gelatin derivatives, hydrophilic cellulose derivatives, polysaccharides such as dextran, gum arabic, agarose and the like, and also synthetic substances such as water-soluble polyvinyl compounds like polyvinyl alcohol and polyvinyl pyrrolidone, acrylamide polymers, etc. Thermoreversable gels are preferable for their simplicity of fabrication. The polymers employed as the reaction layer may be cross-linked, if desired, but care should be taken to avoid deactivation of the antibody by the cross-linker.

The detectable species may comprise conventional labelling means known to the art. Among suitable detectable species mention may be made of radioactive labels, e.g., gamma detection, fluorescent labels, enzyme labels (to provide a colormetric signal), and luminescent labels. In a preferred embodiment, fluorescent material is employed as the detectable species, particularly because of sensitivity of detection.

In a preferred embodiment, the hydrophilic colloid in the reaction layer also contains a permeator to enhance the diffusion constant of the labelled antibody in the polymer matrix, i.e., the permeator effectively increases the pore size of the hydrophilic colloid medium. Preferably, the permeator is a hydrophilic, non-gelling polymer such as polyvinyl pyrrolidone or sorbitol. While not intended to be bound by theory, it is believed that the permeator reduces the degree of hydrogen bonding in the gelled polymer, providing less resistance to the diffusion of the antibody with the detectable species.

If fluorometric detection techniques are employed care should also be taken to avoid the use of a material which can lower the quantum efficiency of flourescence, thus rendering the antibody substantially less detectable.

To illustrate the effectiveness of permeators in the polymer matrix comparative radial diffusion measurements were performed on a wide variety of coated polymer matrices.

EXAMPLE 2

Agarose (SEAKEM LE) solutions were prepared with the below-indicated permeator additives and coated by extrusion on a polystyrene base (TRYCITE) which was subcoated to promote adhesion with a composition comprising 68.3 g of adhesive polymer (RHOPLEX, Rhom and Haas Co., Philadelphia, PA), 5.6 g of a 10% solution of dioctyl malonate, 26.7 g of a 10% colloidal silica dispersion (LUDOX, E. I. DuPont de Namours Company, Wilmington, DE), 40 g of a 10% solution of phthalated gelatin, 3 g of a 50% solution of polynonylphenoxy glycidol (OLIN 10G) and 862 g of water. A 5% solution of sodium fluoresceinate was used as a tracer dye. The coated samples to be tested were mounted by double stick tape to a glass plate and the tests were carried out in a Selectrasol TLC-Solvent Selector System (Schleicher & Schell, Inc. Keene, NH). The tracer dye solution was applied through a porous wick to the center of each test sample for 24 hours in a humid environment to prevent premature evaporation of the solvent. Table 2 summarizes the results.

TABLE 2

| Sample No. | Material/Permeator | Coverage mg/ft² | Dye Spot Diameter (Micrometers) |
|---|---|---|---|
| 1 | agarose | 2000 | 8 |
| 2 | agarose | 1500 | 8 |
| 3 | agarose | 1000 | 8 |
| 4 | agarose/sorbitol | 1000/500 | 13 |
| 5 | agarose/carbowax | 1000/1000 | 11 |
| 6 | agarose/polysucrose | 1000/1000 | 10 |

The carbowax employed was polyethylene glycol, M.W. 3000–37,000 Fisher Scientific Co., Fairhaven, NJ.

The polysucrose was FICOLL 400 sold by Pharmacos Fine Chemicals, Uppsala, Sweden.

Table 2 illustrates the effectiveness of various permeators to increase the rate of diffusion through the agarose layer.

The porous opaque layer is permeable to the diffusing antibody with the detectable species and provides opacity to prevent a false reading by eliminating any possibility of the detection of detectable species other than in the registration layer. In other words, the porous opaque layer prevents detection of the detectable species retained in the reaction layer. For example, in the case of a fluorescent detectable species, the porous opaque layer will absorb in the region of the exciting radiation, e.g., the ultraviolet region, while maintaining reflectivity in the region of the fluorescing radiation, e.g., the visible region. Thus, the exciting radiation will be effectively restrained from reaching the bound label while the emitted radiation from the registration layer is reflected rather than absorbed. The porous opaque layer may comprise a suitable reflecting material in a binder. Preferably, titanium dioxide in agarose is coated at various coverages to provide the desired degree of porosity. As desired, the porous opaque layer may also include suitable additives to improve opacity and reflectance.

Since many pigments process high surface binding coefficients for non-specific absorption of immunoglobulins, it is desirable to pretreat such pigments with another polymer which is strongly absorbed to the surface of the pigment but which has no affinity itself for the immunoreagent.

The following example illustrates the effectiveness of a surface treatment to inhibit undesireable immunoglobulin binding to particulate materials.

EXAMPLE 3

Surface Treatment Process 100 g of titanium dioxide (TiPure R-931, E. I. DuPont de Namours Company, Wilmington, DE) was mixed with 400 g of a 1% solution of photographic grade gelatin Type 9168 (Rousselot Corp., Paris, France) and stirred at 40° C. for 1 hour. At the end of that period the titanium dioxide was separated by low-speed centrifugation. Excess gelatin was removed; the titanium dioxide resuspended in distilled water followed by centrifugation. This gelatin removal step was repeated three times.

EXAMPLE 4

Surface Activity Determination

Samples of pigment (0.3 g) treated according to he procedure of Example 3 were stirred for 1 hour with 3.0 g of labeled immunoglobulin (FITC-antihuman albumin, Atlantic Antibodies, Inc., Scarborough, ME), diluted 1:9 with phosphate buffered saline and then diluted with water to a total of 6.89 g. The mixture was loaded in an ultrafiltration cell with an AMICON XM-3000 membrane filter (AMICON, Inc., Cambridge, MA) and centrifuged at low spped for several minutes. 1 ml of the ultrafiltrate was diluted 1:9 with phosphate buffered saline and the fluorescence intensity was measured with a Beckman 5864 Spectrophotometer Fluorescence Accessory MODEL 196776 (Beckman Instruments, Inc. Fullterton, CA) set up for fluorescence readout.

The control sample was the immunoglobulin solution at the same dilution as the test samples and ultracentrifuged the same as the test samples. Table 3 contains the fluorescence intensity (FI) measurements from the samples normalized to 100% for the control.

TABLE 3

| Sample | F.I. |
|---|---|
| Untreated $TiO_2$ | 4.4 |
| Treated $TiO_2$ (Ex. 3) | 54.4 |
| Control (immunoglobulin solution) | 100.00 |

Table 3 illustrates the effectiveness of pigment treatment in inhibiting immunoglobulin binding.

The registration layer acts as a location to concentrate by immobilization the diffusing antibody with the detectable species. Detection means are employed to measure the quantity of detectable species in this layer. Materials adapted to non-specifically bind, immobilize or "mordant" antibodies are well known in the art. See, for example, Journal of the Reticuloendothelial Society, Vol. 3, p. 29–40 (1966).

While many of the materials known to the art to immobilize or mordant antibodies will function in solution, they appear to be inactivated in a gelled environment such as agarose and, therefore, require special attention to their selection for use in the present invention.

The following non-limiting example illustrates the effectiveness of non-specific adsorption characteristics in the registration layer for the fixation of labeled immunoglobulin.

EXAMPLE 5

A series of coatings were prepared employing agarose as the gelled environment with the below-indicated materials incorporated therein as a discontinuous phase. A surfactant, p-nonylphenoxypolyglycidol, (OLIN 10G) was added as a coating acid. The coatings were evaluated by allowing each coating to contact a fixed volume of labeled antibody solution for exactly 10 min. The antibody solution employed was the same as the one set forth in Example 3. At the end of the contact period the coatings were rinsed in distilled water and air dried at ambient temperatures. Fluorescence (in arbitrary relative units) was measured by the same technique as described in Example 4.

TABLE 4

| Coating No. | Materials | Coverage (mg/ft²) | F.I.($\times 10^4$) |
|---|---|---|---|
| 1 | agarose/starch | 1000/1000 | 1.7 |
| 2 | agarose/polyethylene oxide | 1000/500 | 3.6 |
| 3 | agarose/$TiO_2$ | 1000/500 | 6.7 |
| 4 | agarose/Polymer A/ polyvinyl pyrrolidone | 1000/1000/1000 | 8.3 |
| 5 | agarose/aluminum | 1000/500 | 13.3 |

TABLE 4-continued

| Coating No. | Materials | Coverage (mg/ft$^2$) | F.I.($\times 10^4$) |
|---|---|---|---|
| | oxide | | |

Polymer A was a graft of 4-vinyl pyridine (4VP) and benzyl trimethyl ammonium chloride (TMQ) on hydroxyethyl cellulose (HEC) at a ratio of 2.2 HEC/2.2 4VP/1 TMQ. The starch was soluble starch sold by Mallinkrodt, Inc., Paris, KY. The polyethylene oxide was an emulsion sold under the trade name POLYOX WSR-N-80 by Union Carbide Corp., New York, NY. The titanium dioxide was the same as that described in Example 3. The polyvinyl pyrrolidone was Type NP-K15, sold by GAF Corp., New York, NY. The aluminum oxide (0.3 micrometers) was sold by Fluka Chemical Co., Hauppauge, NY.

Alternatively, an antibody may be precoated in the registration layer to provide the mordanting characteristics. See, for example, U.S. Pat. No. 4,258,001, supra. However, this is not necessary employing the registration layers described in Table 4 since those registration layers are not only effective mordants for the antibody but are also non-specific, i.e., they will bind to substantially all immunoglobulin G's regardless of their source.

The radiation transparent base employed in the present invention is transmissive to the radiation emitted by the detector as well as the detectable species. For example, in a preferred embodiment, the detector will emit exciting radiation and detect fluorescence emitted by the detectable species. As examples of suitable film bases for use as the radiation transparent base mention may be made of materials such as cellulose acetate, polyethylene terephthalate, polycarbonates, and polyvinyl compounds such as polystyrenes. To promote adhesion, it may be preferable to subcoat the film base.

It should also be understood that the novel analytical element of the present invention may include optional layers such as filter layers, timing layers, and the like. For example, a filtering layer may be employed over the spreader layer or reaction layer to remove micromolecules and particulates that might interfere with the analysis. It may also be desirable to provide a timing layer to regulate the delay between antigen contact with the reaction layer and diffusion of the antibody with the detectable species to avoid any false readings as a result of antibody diffusion before the antigen has had an opportunity to bind thereto in the reaction layer. A filtering layer may also be employed to prevent extraneous materials from entering the registration layer.

Turning now to the drawings, FIG. 1 is a cross-sectional view of a preferred element of the present invention. Element 10 is composed of the following layers, in order; spreader layer 12, to which the analyte is applied; reaction layer 14, which contains the antibody with detectable species; interlayer 16, which, as described above, may include timing layers and/or filtering layers; porous opaque layer 18, adapted to isolate the detectable species remaining in the reaction layer from the detectable species in registration layer 20 which registration layer includes a concentration or immobilizing element for the diffusing antibody with detectable species; and radiation transparent layer 22 which functions as a support for element 10 and through which the detector determines the emitted radiation from the detectable species in registration layer 20.

Figure 2:
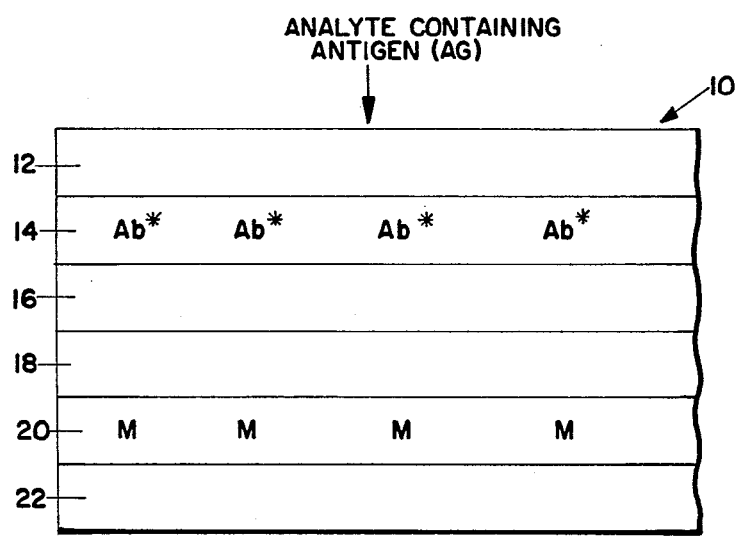
FIG. 2 is a schematic, cross-sectional view of the element of FIG. 1 indicating the location of some of the components in the element prior to contact with the analyte.
Figure 3:
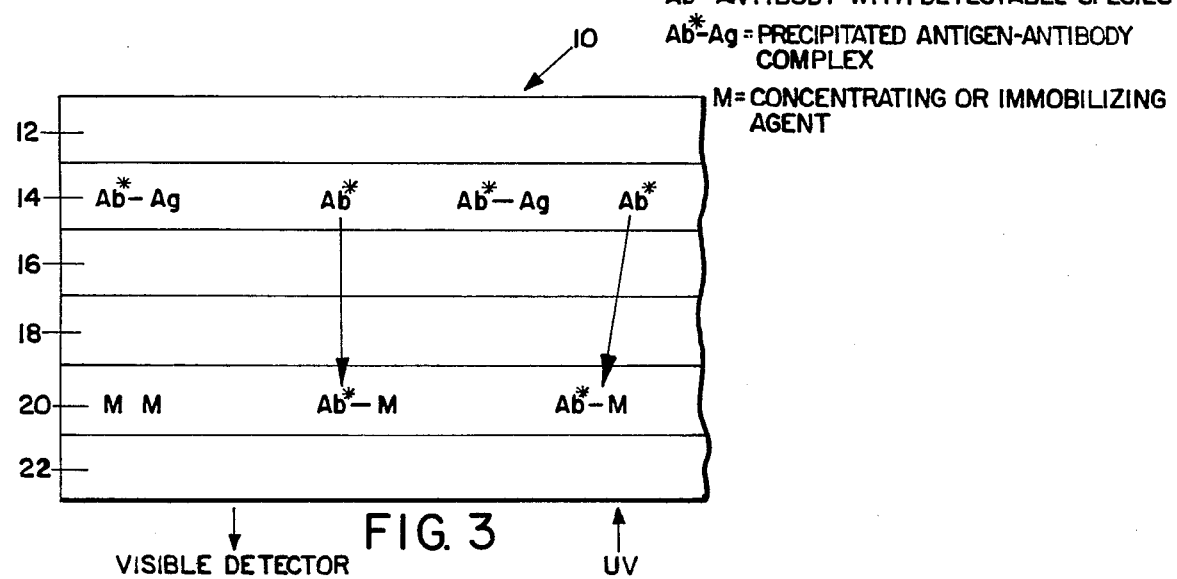
FIG. 3 is a schematic, cross-sectional view of the element of FIG. 2 indicating the location of some of the components in the element subsequent to contact with the analyte.

FIGS. 2 and 3 show the operation of element 10 of FIG. 1. Sample fluid containing analyte, in this case antigen which is the substance under analysis, is applied to spreader layer 12 where a uniform predetermined amount is received and which then diffuses to reaction layer 14. The antigen will associate with a like quantity of antibody located in layer 14 forming a substantially non-diffusing complex. The excess of antibody over antigen, which is normally diffusible through the element in the sample liquid, will diffuse through interlayer 16 and porous opaque layer 18 and become immobilized in registration layer 20 where the detectable species will be activated by incident radiation through the radiation transparent layer 22 and the quantity of detectable species ascertained.

The following non-limiting example illustrates the operation of the element of the present invention.

EXAMPLE 6

10 ml of 0.1% human serum albumin (antigen) (Sigma Chemical Co., St. Louis, MO) and 100 ml of goat anti-human serum albumin IgG fraction labeled with fluorescein isothiocyanate (antibody) (sold by Atlantic Antibodies, Inc., Scarborough, ME) diluted 1:5 in phosphate buffered saline solution were mixed in a test tube. A whitish precipitate was immediately formed. The contents of the test tube was spotted onto an element comprising:

(a) a reaction layer comprising 1000 mg/ft$^2$ of agarose and 1000 mg/ft$^2$ of polyethylene glycol, M.W. 3000–3700 (Fisher Chemical Co., Fasilawa, NJ);

(b) a porous layer substantially opaque to radiation comprising 520 mg/ft$^2$ of titanium dioxide (sold by E. I. DuPont de Namours, Inc., Wilmington DE under the tradename TiPure R-933) pretreated with gelatin and 500 mg/ft$^2$ of agarose;

(c) a registration layer comprising 1000 mg/ft$^2$ of agarose and 100 mg/ft$^2$ polyethylene glycol M.W. 4000; and (d) a 3 mil subcoated polystyrene base (TRICITE sold by Dow Chemical Co., Midland, MI).

After a two hour imbibition period ultraviolet light was shined through the base of the above element and a control element to which no human serum albumin was applied with the goat anti-human serum albumin. In the case of the control a considerable amount of fluorescence was detected indicating a substantial amount of the fluorescein labeled antibody reaching the registration layer while the test sample showed significantly less fluorescence indicating that a substantial amount of fluorescein labeled antibody was immobilized by the antigen and did not reach the registration layer.

Contrary to the kinetic techniques set forth in the prior art described above, the present invention employs an endpoint technique. The term "endpoint technique" as used herein is intended to refer to a delineation based on a chemical reaction yielding a detectable product, the total amount of which remains substantially fixed after some designated period of time over which the reactants are substantially exhausted. An endpoint technique operates with ambient levels of analyte and stoichiometric quantities of reagent and is inherently less sensitive to variations in temperature than kinetic techniques.

The dispacement release mechanisms described in U.S. Pat. Nos. 3,992,158, 4,422,335, and 4,144,306, for example, are inherently kinetic assay systems because a large excess of reagents are necessary to accelerate the reaction to a measurable rate. Kinetic techniques are temperature and time sensitive and require complex instrumentation to determine rate constants.

The novel method and element of the present invention provides inherently faster reaction time since the association reaction rate is orders of magnitude faster than the dissociation which is a necessary prerequisite for displacement release as employed in the above-mentioned patents.

What is claimed is:

1. A multilayer element for the analysis of a liquid containing an analyte comprising a reaction layer which retains a predetermined amount of a diffusible reagent containing a detectable species, said diffusible reagent being present in an amount in excess of that reactable with an analyte to be determined; said reagent adapted to be rendered substantially non-diffusible by said analyte as a function of the concentration of said analyte; a registration layer adapted to receive reagents diffusing thereto; and an insulating layer permeable to said diffusible reagent intermediate said reaction layer and said registration layer, said insulating layer preventing detection of the detectable species retained in the reaction layer.

2. The element of claim 1 which includes a sample spreading layer for receiving the liquid to be analyzed.

3. The element of claim 2 wherein said spreading layer is an isotropically non-fibrous spreading layer.

4. The element of claim 2 wherein said spreading layer is fibrous.

5. The element of claim 1 wherein said detectable species is a fluorescent material.

6. The element of claim 1 wherein said detectable species is a radioactive material.

7. The element of claim 1 wherein said insulating layer is opaque to the radiation from said detectable species.

8. The element of claim 1 wherein said liquid contains antigen (antibody) and said reaction layer contains diffusible antibody (antigen) with a detectable species attached thereto.

9. The element of claim 2 wherein said spreading layer is a fabric.

10. The element of claim 2 wherein said reaction layer comprises agarose.

11. The element of claim 1 wherein said insulating layer comprises titanium dioxide.

12. The element of claim 1 wherein said registration layer comprises agarose.

13. The element of claim 1 wherein said registration layer includes polymeric emulsion.

14. The element of claim 1 including a radiation transparent base carrying said layers.

15. The element of claim 14 wherein said base is polystyrene.

16. A method for analyzing an analyte in a liquid which comprises adding said liquid to an element comprising a plurality of layers including a reaction layer and a registration layer; said reaction layer containing a predetermined amount of a diffusible reagent containing a detectable species, said diffusible reagent being present in an amount in excess of that reactable with an analyte to be determined; said reagent being rendered non-diffusible by said analyte as a function of the concentration of said analyte; said registration layer adapted to receive reagent diffusing thereto; and measuring the quantity of reagent diffusion to said registration layer.

* * * * *